US010828052B2

(12) United States Patent
Miller

(10) Patent No.: US 10,828,052 B2
(45) Date of Patent: Nov. 10, 2020

(54) ULTRASONIC AND/OR SONIC TONGUE-CLEANING TOOL KIT

(71) Applicant: Richard A. Miller, McLean, VA (US)

(72) Inventor: Richard A. Miller, McLean, VA (US)

( * ) Notice: Subject to any disclaimer, the term of this patent is extended or adjusted under 35 U.S.C. 154(b) by 74 days.

(21) Appl. No.: 15/976,934

(22) Filed: May 11, 2018

(65) Prior Publication Data

US 2018/0325539 A1      Nov. 15, 2018

Related U.S. Application Data

(60) Provisional application No. 62/504,984, filed on May 11, 2017.

(51) Int. Cl.
  *A61B 17/24*   (2006.01)
  *A61B 17/00*   (2006.01)

(52) U.S. Cl.
  CPC .. *A61B 17/244* (2013.01); *A61B 2017/00398* (2013.01); *A61B 2017/00402* (2013.01)

(58) Field of Classification Search
  CPC .................................................. A61B 17/244
  See application file for complete search history.

(56) References Cited

U.S. PATENT DOCUMENTS

| 1,658,706 | A | * | 2/1928 | Carrott | A61C 15/02 |
| | | | | | 132/309 |
| 3,368,280 | A | | 2/1968 | Friedman et al. | |
| 3,375,583 | A | | 4/1968 | Blank et al. | |
| 3,488,851 | A | | 1/1970 | Haydu | |
| 4,176,454 | A | | 12/1979 | Hatter et al. | |
| D285,253 | S | * | 8/1986 | Audette | D24/147 |
| 5,577,911 | A | * | 11/1996 | Garfinkel | A61C 17/20 |
| | | | | | 433/119 |
| 5,766,193 | A | | 6/1998 | Millner | |
| 5,853,290 | A | * | 12/1998 | Winston | A61C 17/20 |
| | | | | | 433/86 |
| 6,440,149 | B1 | | 8/2002 | Potti | |
| 6,895,624 | B2 | | 5/2005 | Fischer et al. | |
| D628,291 | S | * | 11/2010 | Palmer | D24/135 |
| 8,202,286 | B1 | | 6/2012 | Suzman | |
| 2003/0167582 | A1 | * | 9/2003 | Fischer | A61B 17/244 |
| | | | | | 15/22.1 |

(Continued)

FOREIGN PATENT DOCUMENTS

| WO | 0001311 | 1/2000 |
| WO | 0234145 | 5/2002 |

*Primary Examiner* — Todd J Scherbel
(74) *Attorney, Agent, or Firm* — John Rizvi; H. John Rizvi—The Patent Professor®

(57) ABSTRACT

There is disclosed a tool kit including differently sized and shaped tongue-cleaning working tips. The working tips generally include a distal working blade for engagement with the surface of the tongue. In some embodiments, the distal working blades are planar and may include one or more bends between planar sections or portions. In other embodiments of the tongue-cleaning working tips, the working blades are curved. The tongue-cleaning working tips may optionally include a proximal mounting stem extending proximally from the distal working blade to allow for better access to certain regions of the tongue. Additionally, the distal working blades of the tongue-cleaning working tips may be tapered to further reach desired areas of the tongue.

19 Claims, 15 Drawing Sheets

(56) References Cited

U.S. PATENT DOCUMENTS

| | | |
|---|---|---|
| 2004/0040572 A1 | 3/2004 | Chodorow |
| 2008/0209650 A1 | 9/2008 | Brewer et al. |
| 2009/0131960 A1 | 5/2009 | Tanaka |
| 2011/0010875 A1 | 1/2011 | Iwahori et al. |
| 2011/0289707 A1* | 12/2011 | Schaefer ............ A46B 15/0002 15/105 |
| 2015/0182240 A1 | 7/2015 | Wawiluk et al. |
| 2016/0051271 A1* | 2/2016 | Bock ................... A61B 17/244 606/161 |

\* cited by examiner

ULTRASONIC AND/OR SONIC TONGUE-CLEANING TOOL KIT

CROSS-REFERENCE TO RELATED APPLICATION

This application claims the benefit of U.S. Provisional Patent Application Ser. No. 62/504,984, filed on May 11, 2017, which is incorporated by reference herein in its entirety.

FIELD OF THE INVENTION

The present invention relates generally to oral hygiene devices, and more particularly, to a set of devices or tools configured to scrape and clean away harmful and malodorous bacteria and other malodorous compounds present on the dorsum of the tongue, and thereby reduce or eliminate bad breath (halitosis).

BACKGROUND OF THE INVENTION

Bad breath, or halitosis, consists in a malodorous emanation coming from the mouth and is one of the most common complaints of people seeking dental treatment. Population estimates of between 5 and 50% are thought to have bad breath.

Many over-the-counter treatments are available to treat bad breath. These may include mouthwashes, flavored toothpastes, gums, mints, etc. However, most of these treatments only cover or mask the odor without eliminating the underlying causes of bad breath.

It has been determined that one of the predominant cause of the malodorous emanations responsible for bad breath arise from a layer or biofilm of decaying or putrefying anaerobic bacteria that builds up on and mechanically attaches to the surface of a person's tongue, and especially to the dorsal surface of the tongue. Other malodorous contaminants or compounds present in the form of a biofilm may include desquamated epithelial cells, white blood cells, dead red blood cells, proteins from saliva, mucous from the pharyngeal and sinus regions, gingival secretions, etc.

It has also been determined that mechanical removal of the biofilm of contaminants results in a significant reduction of the malodorous emanations. Commonly available manually operable devices such as tongue scrapers, tongue cleaners, etc. are available over the counter to attempt to remove the contaminants. However, these devices are seemingly incapable of curing the situation as they are not capable of reaching the deeper areas and layers of the biofilm to remove all the contaminants. Additionally, given the varying nature of the posterior-to-anterior and side-to-side shape of the human tongue, these devices simply cannot reach all of the areas of the tongue containing the contaminants.

To date, the dental profession has found no cure for bad breath. The official position of the American Dental Association centers around "regular" dental cleanings, avoiding odorous foods, daily oral hygiene, and the use of mouthwashes and other odor-covering aids.

Accordingly, there remains a need for an effective and efficient method and system capable of successfully reducing or eliminating the cause of halitosis, i.e. removing the biofilm down to the base of the tongue to remove the offending bacterial and other malodorous contaminants and compounds.

SUMMARY OF THE INVENTION

The present invention is directed to an effective and efficient tool kit and method for removing a malodorous biofilm of bacteria and other noxious compounds from the surface of the tongue. The tool kit includes differently sized and shaped tongue-cleaning tools and an ultrasonic- or sonic-generating hand piece for coupling with the various tools. The tools generally include a tongue-cleaning distal working tip or blade for engagement with the surface of the tongue. In some embodiments, the tongue-cleaning working blades are planar or plate-shaped and may optionally include one or more bends. In other embodiments of the tongue-cleaning working tips, the tongue-cleaning distal working blades are curved. The working tips may include a proximal mounting stem which may be straight or have bends formed therein to better access certain regions of the tongue. Additionally, the tongue-cleaning distal working blades of the tongue-cleaning tools may be tapered to further reach desired areas of the tongue.

In a first implementation of the invention, a tongue-cleaning tool kit for removing a biofilm from a surface of a tongue is provided, the tongue-cleaning tool kit comprising at least one tongue-cleaning working tip. Each working tip includes a respective distal working blade configured to scrape a biofilm from a surface of a tongue. The at least one tongue-cleaning working tip includes an angled, tongue-cleaning working tip, the distal working blade of which is elongated in a front-to-back, longitudinal direction and comprises a planar, proximal blade portion and a planar, distal blade portion connected to the proximal blade portion at a bend portion and arranged forming an angle relative to the proximal blade portion. The at least one tongue-cleaning working tip further includes a curved, tongue-cleaning working tip, the distal working blade of which is curved and comprises a convex top surface and a concave bottom surface.

In a second aspect, the distal blade portion of the angled, tongue-cleaning working tip can be longer than the proximal blade portion of the angled, tongue-cleaning working tip.

In another aspect, the distal working blade of the angled, tongue-cleaning working tip can include a first side edge and a second side edge extending longitudinally and parallel to one another.

In another aspect, the distal working blade of the angled, tongue-cleaning working tip can be formed as an angled plate having a constant thickness and flat and angled top and bottom surfaces separated by the aforementioned constant thickness.

In another aspect, the distal working blade of the angled, tongue-cleaning working tip can extend distally from a proximal mounting stem.

In another aspect, the proximal mounting stem can include a proximal end extending in a same direction as the proximal blade portion of the angled, tongue-cleaning working tip. For example, the proximal mounting stem can be straight and extends in said same direction from the proximal end of the proximal mounting stem to a distal end of the proximal mounting stem which is connected to the proximal blade portion of the angled, tongue-cleaning working tip.

In another aspect, the proximal mounting stem can include a proximal end arranged forming an angle with the proximal blade portion of the angled, tongue-cleaning working tip. For example, the proximal mounting stem can include a proximal stem portion and a distal stem portion forming an angle with one another, wherein the proximal stem portion provides the proximal end of the proximal mounting stem and the distal stem portion is connected to and arranged in a same direction with the proximal blade portion of the angled, tongue-cleaning working tip.

In another aspect, the distal working blade of the curved, tongue-cleaning working tip can have a varying radius of curvature. In some embodiments, the distal working blade of the curved, tongue-cleaning working tip can include a distal working tip which is curved reardwardly towards a proximal end of said distal working blade of the curved, tongue-cleaning working tip.

In another aspect, the at least one tongue-cleaning working tip can further include a flat, tongue-cleaning working tip, the distal working blade of which is plate-shaped. In some embodiments, the distal working blade of the flat, tongue-cleaning working tip can extend distally from a proximal mounting stem. For example, the proximal mounting stem can include a proximal stem portion and a distal stem portion forming an angle with one another, wherein the proximal stem portion provides a proximal end of the proximal mounting stem and the distal stem portion is connected to and arranged in a same direction with the proximal blade portion of the flat, tongue-cleaning working tip.

In another aspect, the distal working blade of the curved, tongue-cleaning working tip can be tapered from a wider proximal edge to a narrower distal edge thereof.

In another aspect, the tongue-cleaning tool kit can further include a hand piece configured to carry one or more working tips of the at least one tongue-cleaning working tip, the hand piece further configured to produce ultrasonic and/or sonic vibrations and transfer the vibrations to the one or more working tips. In some embodiments, the hand piece can be piezoelectric or magnetostrictive.

In another implementation of the invention, the present invention consists of a method of mechanically removing a biofilm from a surface of a tongue, comprising the steps of:

providing a hand piece capable of generating vibrations in the ultrasonic and/or sonic frequency range, said hand piece having a coupling portion and a tongue-cleaning working tool removably attached to said coupling portion of said hand piece, the tongue-cleaning tool including a distal working blade having tongue engaging edge;

positioning said tongue engaging edge of said tongue-cleaning tool against a surface of the tongue containing the biofilm;

energizing the hand piece to transmit vibrations in the ultrasonic and/or sonic range to the tongue engaging edge through the distal working blade of the tongue-cleaning tool; and drawing the tongue engaging edge across the surface of the tongue containing the biofilm to break up the biofilm.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a convenient and efficient tongue-cleaning system and method that can be used to clean off a biofilm of putrefying anaerobic bacteria or other noxious compounds from various locations on a tongue. The tongue-cleaning system of the present invention comprises a tool kit including five tools, or subsets thereof, which will be described in detail hereinafter. The tongue-cleaning method of the present invention refers to a method of removing the biofilm from a tongue using the tool kit.

Figure 1:
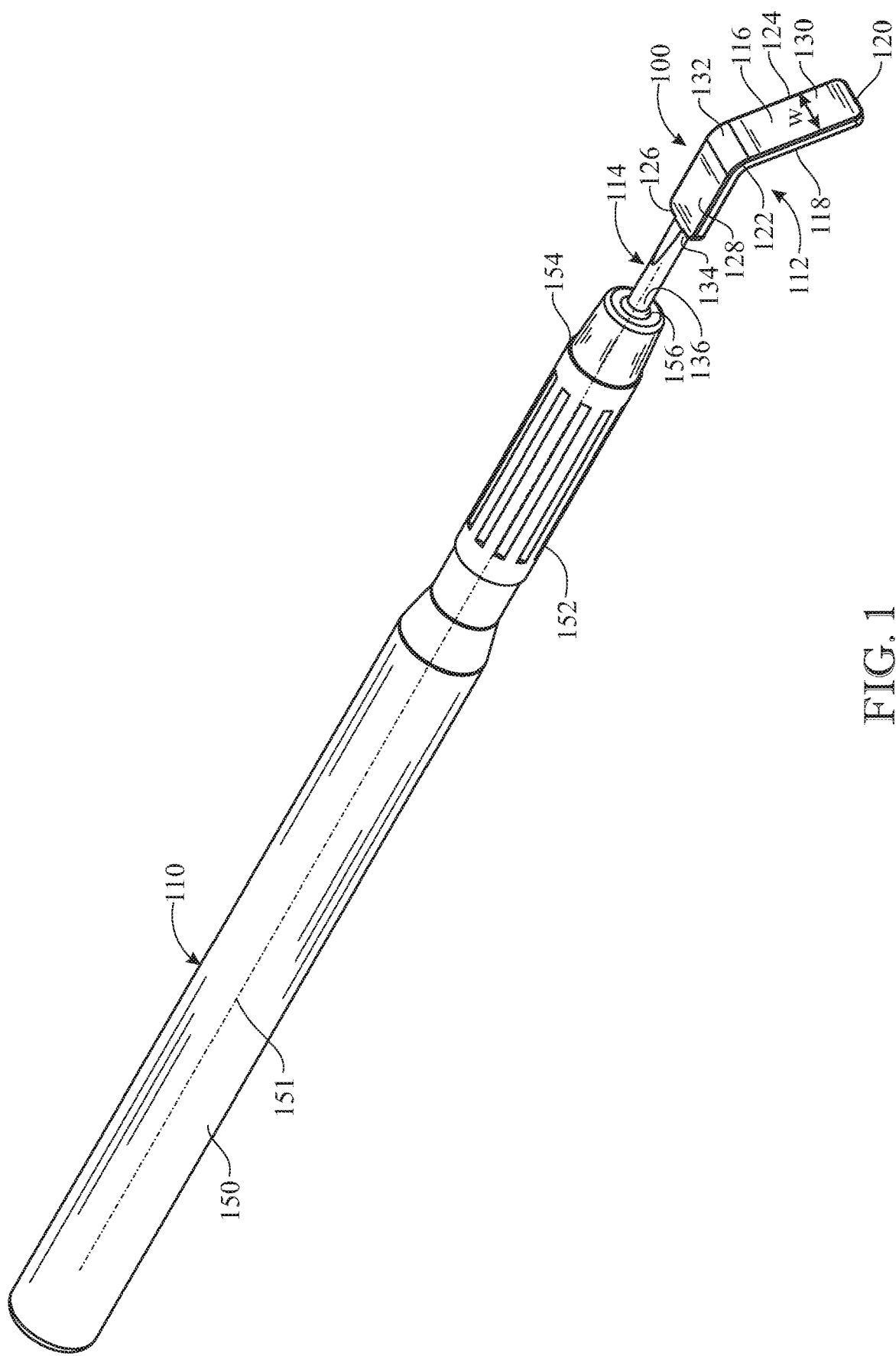
FIG. 1 presents a top, front isometric view of an ultrasonic, handheld tongue-cleaning tool comprising an ultrasonic hand piece carrying a first tongue-cleaning working tip in accordance with an illustrative embodiment of the present invention, for use in cleaning a patient's tongue.
Figure 2:
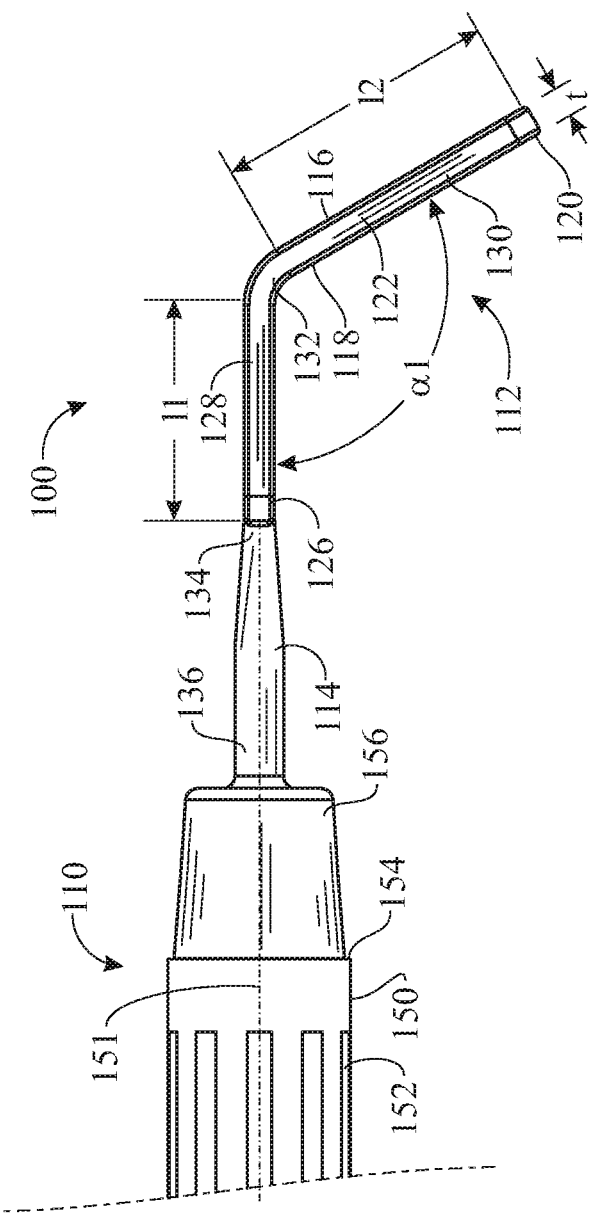
FIG. 2 presents a partial, enlarged side elevation view of the tongue-cleaning tool of FIG. 1, illustrating the tongue-cleaning working tip and a distal portion of the hand piece.

Referring initially to FIGS. 1 and 2, a first tongue-cleaning working tip 100 is illustrated in accordance with an exemplary embodiment of the present invention, configured as an elongated scraper. As shown, the tongue-cleaning working tip 100 is provided for use with an ultrasonic hand piece 110, the tongue-cleaning working tip 100 and ultrasonic hand piece 110 forming a tongue-cleaning, handheld ultrasonic tool.

The ultrasonic hand piece 110 is provided to supply a source of ultrasonic vibration to the tongue-cleaning working tip 100 for use in scraping unwanted biofilm off of a person's tongue. The ultrasonic hand piece 110 generally includes an elongate body portion 150 extending along a longitudinal direction 151. The elongate body portion 150 comprises a grasping portion 152 extending along all or part of the elongate body portion 150. The elongate body portion 150 terminates in a distal end 154 having an opening or connector 156 for releasably receiving and securing the tongue-cleaning working tip 100 within the distal end 154 of the hand piece 110. The releasable connector 156 allows for exchange of differing tongue-cleaning tools as discussed in more detail herein below. Alternatively, the tongue-cleaning working tip 100 may be fixedly or releasably retained within the distal end 154 of the ultrasonic hand piece 110 by friction fit, a snap-on connection, permanently affixed, threaded or any other suitable know method of coupling the tongue-cleaning working tip 100 to the hand piece 110.

The ultrasonic hand piece 110 may utilize various types of ultrasonic generation technologies. For example, the hand piece 100 may be piezoelectric or magnetostrictive, which are two types of ultrasonic tools typically used in dentistry which differ in the way electrical energy (usually provided by a power source external to the hand piece) is converted into vibrational energy in the ultrasonic range. In at least one embodiment (such as those depicted in the drawings), the ultrasonic hand piece 110 is magnetostrictive and includes a magnetostrictive drive system having an insert placed into the body portion 150 and which includes a magnetostrictive stack, a transducer, and the working tip 100 receiving ultrasonic energy from the transducer. In an alternative embodiment, the ultrasonic hand piece 110 is provided with a piezoelectric ultrasonic drive system as is known in the art, and the working tip 100 receiving ultrasonic energy from the piezoelectric hand piece 110.

The tongue-cleaning working tip 100 can generally include a distal working blade 112 and a proximal mounting stem 114 extending proximally from the distal working blade 112. The distal working blade 112 is provided to scrape a biofilm off of a tongue and the proximal mounting stem 114 transfers ultrasonic vibration generated by the ultrasonic hand piece 110 to the distal working blade 112.

The distal working blade 112 generally includes an upper surface 116, a lower surface 118 and a distal working edge or treatment edge 120. The treatment edge 120 may be sharp, bluntly sharpened or relatively smooth. Additionally, the treatment edge 120 may be flat, angled or curved including a concave or convex face. The distal working blade 112 additionally includes first and second side edges 122 and 124, respectively, and a proximal edge 126. The mounting stem 114 extends proximally from the proximal edge 126 of the working blade 112 and is affixed to the hand piece 110. As shown, the working blade 112 has a first or proximal blade portion 128 connected to the mounting stem 114 and a distal blade portion 130 extending from a bend portion 132 and at an angle α1 from the proximal blade portion 128. The distal working blade 112 has a thickness "t" and a constant width "w". In some embodiments, such as in the present embodiment, the thickness "t" can be generally constant. Alternatively or additionally, the width "w" also may or may not be constant (for example, the width "w" may not be constant, and the distal working blade 112 may taper). The proximal blade portion 128 has a length "l1" and the distal blade portion 130 has a length "l2"; in some embodiments, as shown, the length "l2" of the distal blade portion 130 may be greater than the length "l1" of the proximal blade portion 120. While not specifically shown, the tongue-cleaning working tip 100, including the distal working blade 112 and the proximal mounting stem 114, may be provided with a through hole or bore for conveying cleansing, cooling and/or flushing fluid from the ultrasonic hand piece 110 to one or more ports formed in the distal working edge 120 of the tongue-cleaning working tip 100 for flushing away loose biofilm and cooling adjacent tissue as described in more detail hereinafter.

In some embodiments, as shown, the proximal working stem 114 is generally circular in cross-section and includes a distal end 134 extending from the proximal edge 126 of the distal working blade 112 and a proximal end 136 insertable into and extending distally from the ultrasonic hand piece 110 in a manner described hereinafter. The proximal working stem 114 may be formed integrally with the distal working blade 112 or may be formed separately and subsequently attached using known methods such as, for example, welding, gluing, etc. As shown in the figures, the proximal end 136 of the proximal mounting stem 114 extends in a same direction as the proximal blade portion 128 of the angled, tongue-cleaning working tip 100. More specifically, the proximal mounting stem 114 (including its proximal end 136) of the present embodiment is straight and extends in the longitudinal direction 151 of the elongate body portion 150 of the ultrasonic hand piece 110, as does the proximal blade portion 128 of the angled, tongue-cleaning working top 100.

The angle α1 between the distal blade portion 130 and the proximal blade portion 118 of the distal working blade 112 (which is the same as the angle formed between the distal blade portion 130 and the longitudinal direction 151 along which the grasping portion 152 of the elongate body portion 150 of the ultrasonic hand piece 110 extends) is within the range from 10 to 175 degrees, and preferably from 35 to 165 degrees, and more preferably from 120 to 160 degrees.

The tongue-cleaning working tip 100 is sized and shaped for scraping mixed areas of the tongue's anatomy, especially in the middle area of the tongue where many large papillae are interspersed with much smaller ones, as best described below.

The tongue-cleaning working tip 100, and all subsequently described tongue-cleaning working tips 200, 300, 400 and 500, may be formed from any appropriate material such as, but not limited to, metallic materials such as, but not limited to, stainless steels, etc. Preferably, the material forming the tongue-cleaning working tip 100 is one suitable for sterilization through various known methods including sterilization within an autoclave system.

It should be noted that, when provided together, the tongue-cleaning working tip 100, along with the tongue-cleaning working tips 200, 300, 400 and 500 that will be subsequently described, form an ultrasonic tongue-cleaning tool kit for scraping off a biofilm from various areas of a patient's tongue. The tongue-cleaning working tips may come together with the ultrasonic hand piece 110 and may be interchangeably attached to the ultrasonic hand piece 110. Alternatively, some or all of the tongue-cleaning working tips may come permanently attached or integrally formed with a corresponding, dedicated ultrasonic hand piece 110.

Figure 3:
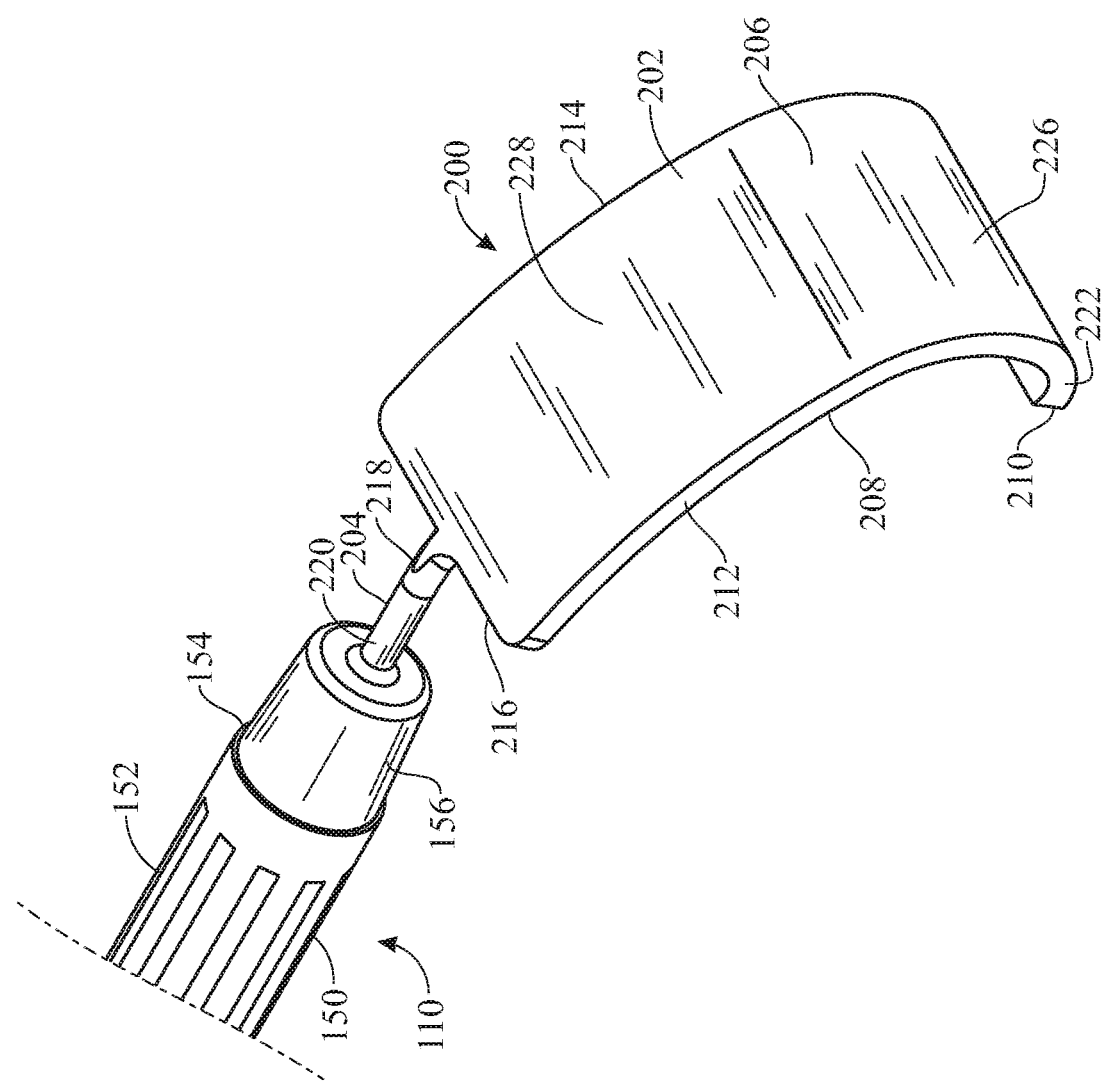
FIG. 3 presents a top, front isometric view of an ultrasonic, handheld tongue-cleaning tool comprising an ultrasonic hand piece carrying a second tongue-cleaning working tip in accordance with an illustrative embodiment of the present invention, for use in cleaning a patient's tongue.
Figure 4:
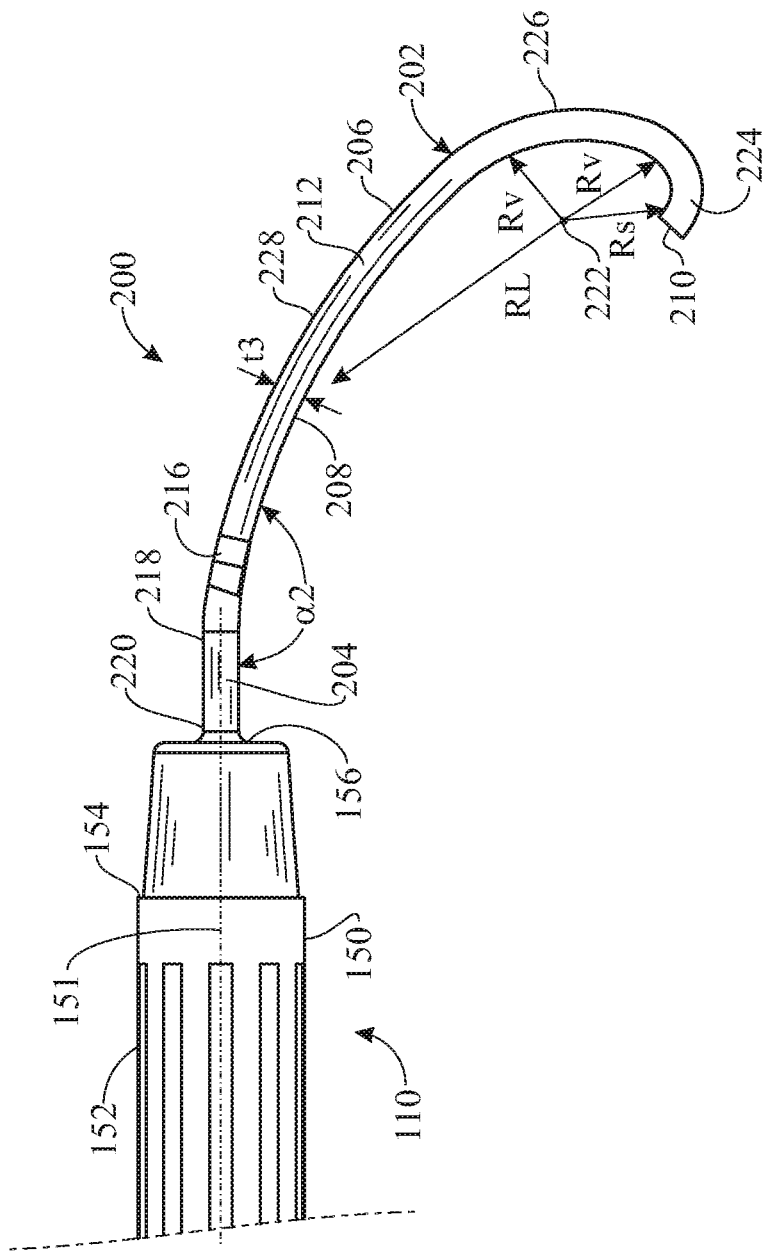
FIG. 4 presents a side elevation view of the tongue-cleaning tool of FIG. 3, illustrating the tongue-cleaning working tip and a distal portion of the hand piece.

Referring to FIGS. 3 and 4, there is disclosed a second tongue-cleaning working tip 200 for use with an ultrasonic hand piece, such as with the above described ultrasonic hand piece 110, to jointly form a tongue-cleaning, ultrasonic handheld tool. The tongue-cleaning working tip 200 can generally include an arcuate or progressively curved distal working blade 202 and a proximal mounting stem 204 extending proximally from the distal working blade 202. The distal working blade 202 includes an upper surface 206, a lower surface 208 and first and second side edges 212 and 214. The distal working blade 202 also has a proximal edge 216 which is connected to a distal end 218 of the mounting stem 204 and a distal working edge 210. A proximal end 220 of the mounting stem 204 is provided for coupling the tongue-cleaning working tip 200 to the ultrasonic hand piece 110 in the manner described herein above with regard to the mounting stem 114 of tongue-cleaning working tip 100.

In this embodiment, as best shown in FIG. 4, the distal working blade 202 is progressively curved having a varying radius "Rv" about a center 222. The radius Rv reduces or tightens from a largest radius "RL" extending from the center 222 to the proximal edge 216 of the distal working blade 202 to a smallest or tightest radius "Rs" extending from the center 222 to the distal working edge 210. This tightening of the radius may form a curved or looped distal portion 226 of the distal working blade 202 which ends in a lip 224 at the distal working edge 210 which is curved back towards the proximal edge 216. This facilitates scraping the posterior most part of a tongue, including the last ⅓ to ⅕ of the tongue and onto the lingual tonsil where it is attached to the pharynx. Alternative embodiments are contemplated in which a proximal portion 228 of the distal working blade 202 is flat (i.e., not curved) and only the looped distal portion 226 is curved, in the manner illustrated herein, i.e. curved back towards the proximal edge 216 and ending in a lip 224. In some embodiments, the first and/or second side edges 212 and 214 can be curved or looped inward, similarly to the looped distal portion 226.

As shown in FIG. 4, the slightly curved (or alternatively flat) proximal portion 228 of the distal working blade 112 forms an angle α2 with the longitudinal direction 151 along which the grasping portion 152 of the elongate body portion 150 of the ultrasonic hand piece 110 extends. Angle α1 is within the range from 10 to 175 degrees, and preferably from 35 to 165 degrees, and more preferably from 120 to 160 degrees.

Figure 5:
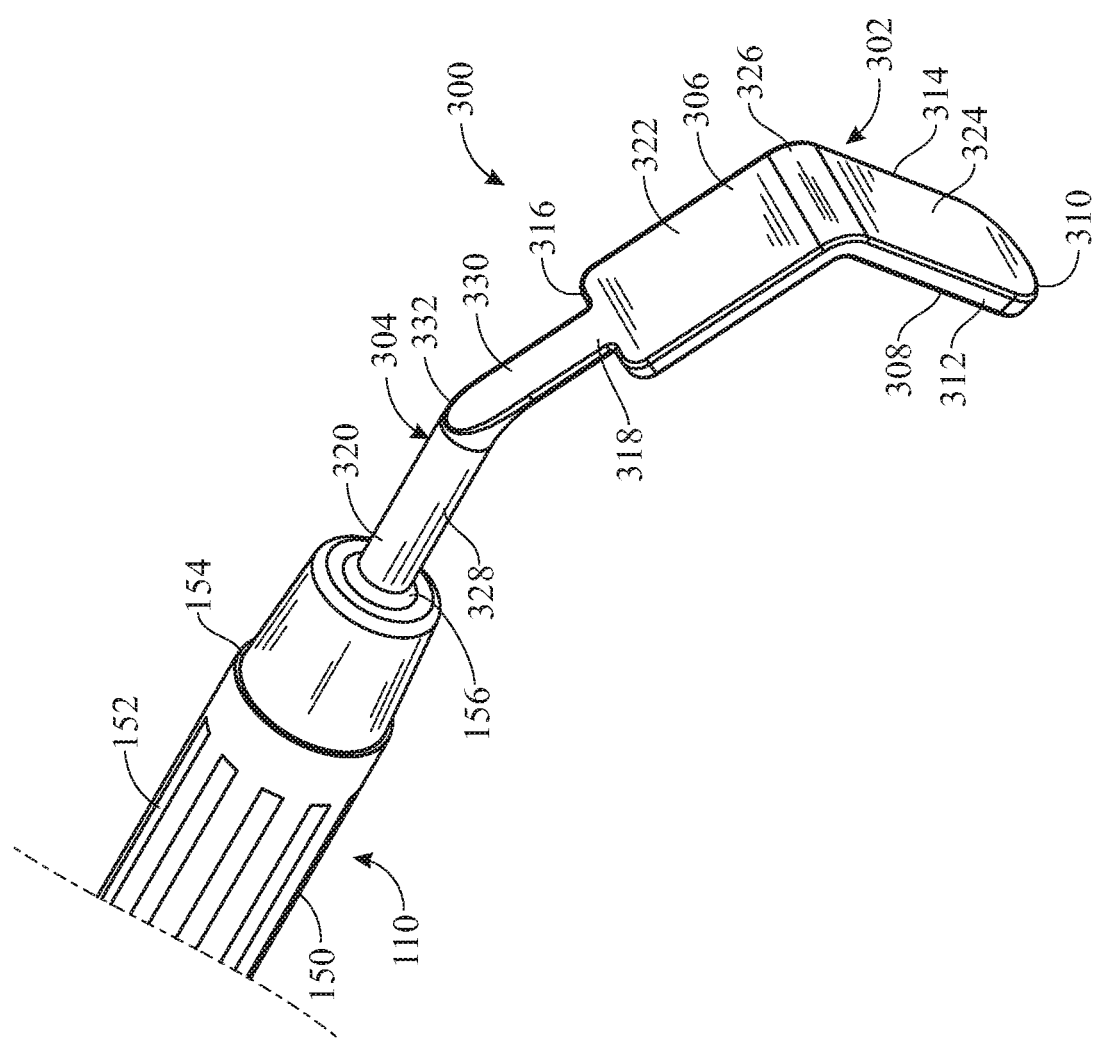
FIG. 5 presents a top, front isometric view of an ultrasonic, handheld tongue-cleaning tool comprising an ultrasonic hand piece carrying a third tongue-cleaning working tip in accordance with an illustrative embodiment of the present invention, for use in cleaning a patient's tongue.
Figure 6:
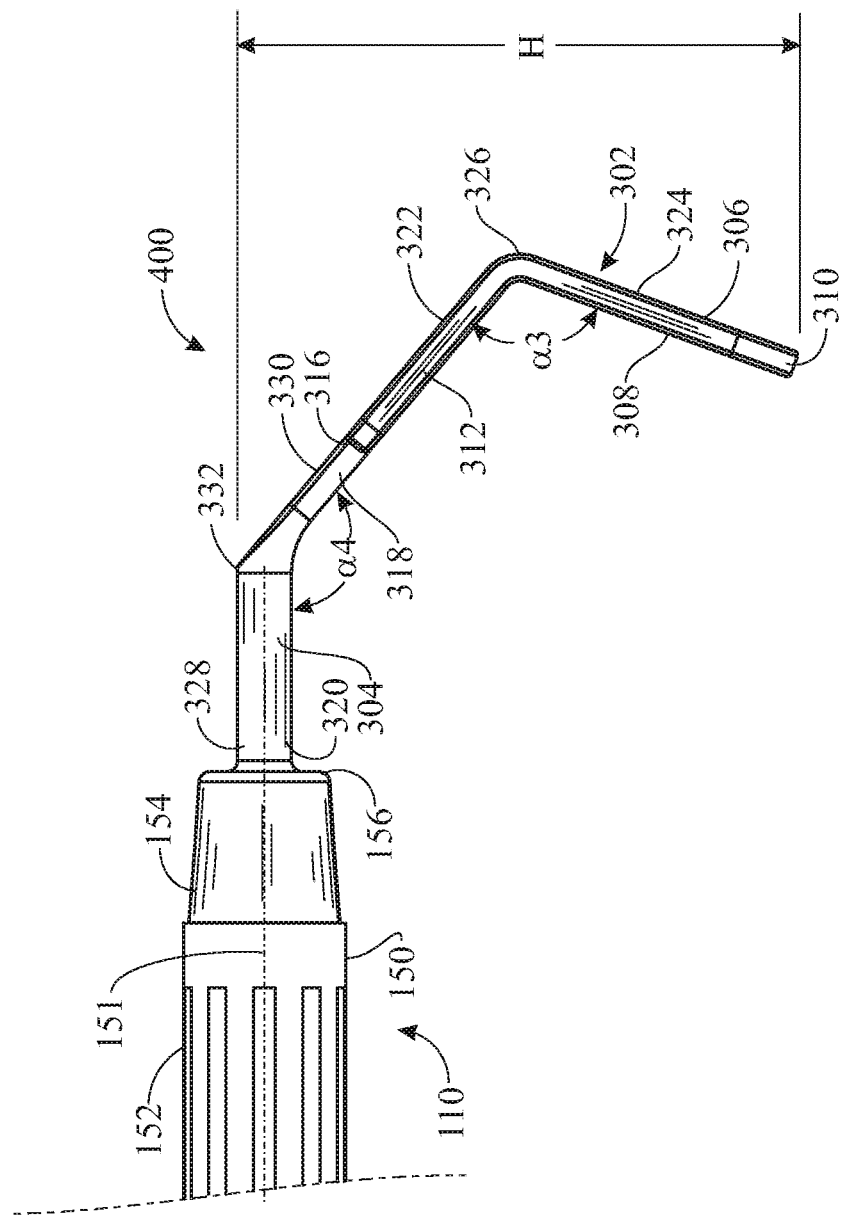
FIG. 6 presents a side elevation view of the tongue-cleaning tool of FIG. 5, illustrating the tongue-cleaning working tip and a distal portion of the hand piece.

With reference to FIGS. 5 and 6, there is disclosed a third tongue-cleaning working tip 300 for use in scraping a middle area of the tongue that attaches to the pharynx at the back of the tongue. The tongue-cleaning working tip 300 generally includes a distal working blade 302 and a proximal mounting stem 304 extending from the distal working blade 302. The distal working blade 302 includes an upper surface 306, a lower surface 308 and a curved or arcuate distal working tip or edge 310. The distal working blade 302 further includes first and second side edges 312 and 314, respectively, and a proximal edge 316. The mounting stem 304 includes a distal end 318 extending from the proximal edge 316 of the working blade 302 and a proximal end 320 releasably attachable or permanently attached to the ultrasonic hand piece.

Similarly to the first tongue-cleaning working tip 100 described hereinabove, the distal working blade 302 of the third tongue-cleaning working tip 300 includes a proximal blade portion 322 and a distal blade portion 324 extending from a blade bend 326 and at an angle α3 (FIG. 6) relative to the proximal blade portion 322, with the angle α3 being within the range from 30 to 175 degrees, and preferably from 45 to 150 degrees, and more preferably from 90 to 120 degrees. In this embodiment, the tongue-cleaning working tip 300 includes multiple or compound bends to allow the tool to reach differing areas of the tongue. Specifically, on one hand, the proximal mounting stem 304 includes a proximal stem portion 328 and a distal stem portion 330 angled relative to each other at a stem bend 332 and at an angle α4, which matches the angle formed by the proximal blade portion 322 and the longitudinal direction 151 of the grasping portion 152 of the elongated body portion 150 of the ultrasonic hand piece 110 (since the proximal stem portion 328 is aligned with or formed in the same direction as the grasping portion 152, and the proximal blade portion 322 is aligned or formed in the same direction as the distal stem portion 330). Angle α4 is within the range from 45 to 175 degrees, and preferably from 90 to 160 degrees, and more preferably from 130 to 160 degrees. It should be noted that, as can be seen in FIG. 5, the distal stem portion 330 is generally planar while the proximal stem portion 328 has a generally circular cross-section. When formed separately, the distal stem portion 330 may be a flat portion of the stem 304 or may be formed as a proximal extension of the proximal blade portion 322, and may be arranged in the same direction as the proximal blade portion 322, as shown. Including the multiple or compound bends, the overall height "H" of the tongue-cleaning working tip 300 is nevertheless small enough to allow the tongue-cleaning working tip 300 to easily and comfortably fit and be manipulated within a patient's mouth to avoid any damage or discomfort.

Figure 7:
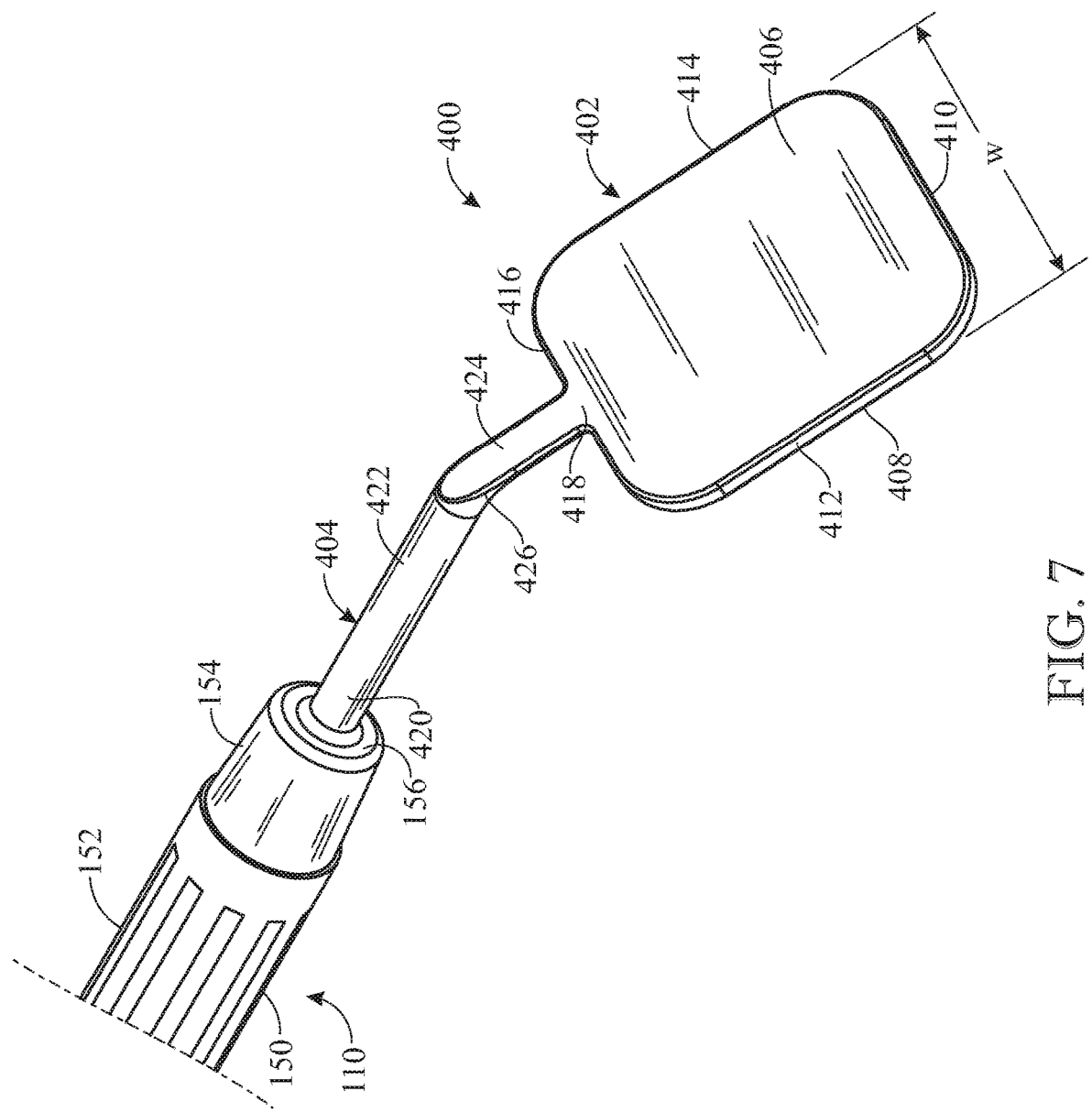
FIG. 7 presents a top, front isometric view of an ultrasonic, handheld tongue-cleaning tool comprising an ultrasonic hand piece carrying a fourth tongue-cleaning working tip in accordance with an illustrative embodiment of the present invention, for use in cleaning a patient's tongue.
Figure 8:
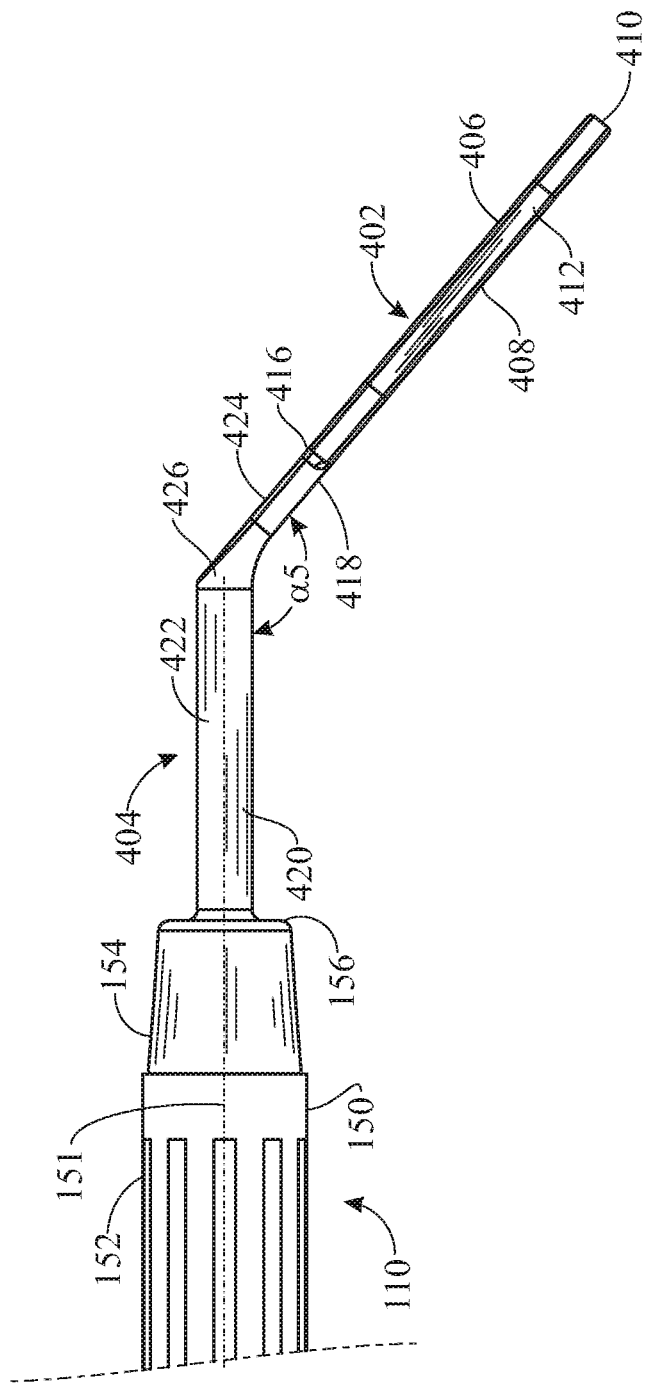
FIG. 8 presents a side elevation view of the tongue-cleaning tool of FIG. 7, illustrating the tongue-cleaning working tip and a distal portion of the hand piece.

Referring to FIGS. 7 and 8, there is disclosed a fourth tongue-cleaning working tip 400 for use with an ultrasonic hand piece, such as ultrasonic hand piece 110. The tongue-cleaning working tip 400 includes a generally rectangular, planar or plate-shaped, distal working blade 402 and a proximal mounting stem 404 extending proximally from the distal working blade 402. The distal working blade 402 is particularly suitable for use in scraping the anterior most two-thirds to four-fifths of the tongue. The distal working blade 402 has an upper surface 406, an opposite, lower surface 408 and a distal working tip or edge 410. The distal working blade 402 additionally includes a first side edge 412, an opposite, second side edge 414 and a proximal edge 416 opposite to the distal edge 410. The distal edge 410 can be straight, as shown, or concave with the concavity facing the proximal end such that when pulled proximally, the concavity will adjust to an outer convex surface of the tongue and scrape along the tongue. The corners or side edges of the distal edge can be sharp; alternatively, the corners or side edges of the distal edge can be rounded (as shown) and smoothed off. As with prior working tips, the size including width, lengths and heights of the tongue-cleaning working tip 400 is sized to comfortably fit in a patient's mouth. The width W of the distal working blade 402 should not exceed two (2) inches, which is about the maximum width of a patient's tongue. In some embodiments, much smaller widths Won the order of ¾" to ½" and even as small as 1/16" are contemplated.

The mounting stem 404 includes a distal end 418 and a proximal end 420. The distal end 418 of the mounting stem 404 is connected to the proximal edge 416 of the working blade 402 and the proximal end 420 of the mounting stem 404 is coupled to the opening or connector 156 of the ultrasonic hand piece 110.

Similarly to the third tongue-cleaning working tip 300, the mounting stem 404 of the fourth tongue-cleaning working tip 400 includes a proximal stem portion 422 and a distal stem portion or blade extension 424. The proximal and distal stem portions 422 and 424 are connected through a stem bend 426 forming an angle α5, which is within the range from 10 to 175 degrees, and preferably from 35 to 165 degrees, and more preferably from 120 to 160 degrees. The distal stem portion 424 can be coplanar or arranged in a same direction (i.e. forming an angle of 0 degrees) with the distal working blade 402, as shown. Thus, angle α5 also matches the angle formed between the distal working blade 402 and the longitudinal direction 151 of the grasping portion 152 of the elongate body portion 150 of the ultrasonic hand piece 110.

Figure 9:
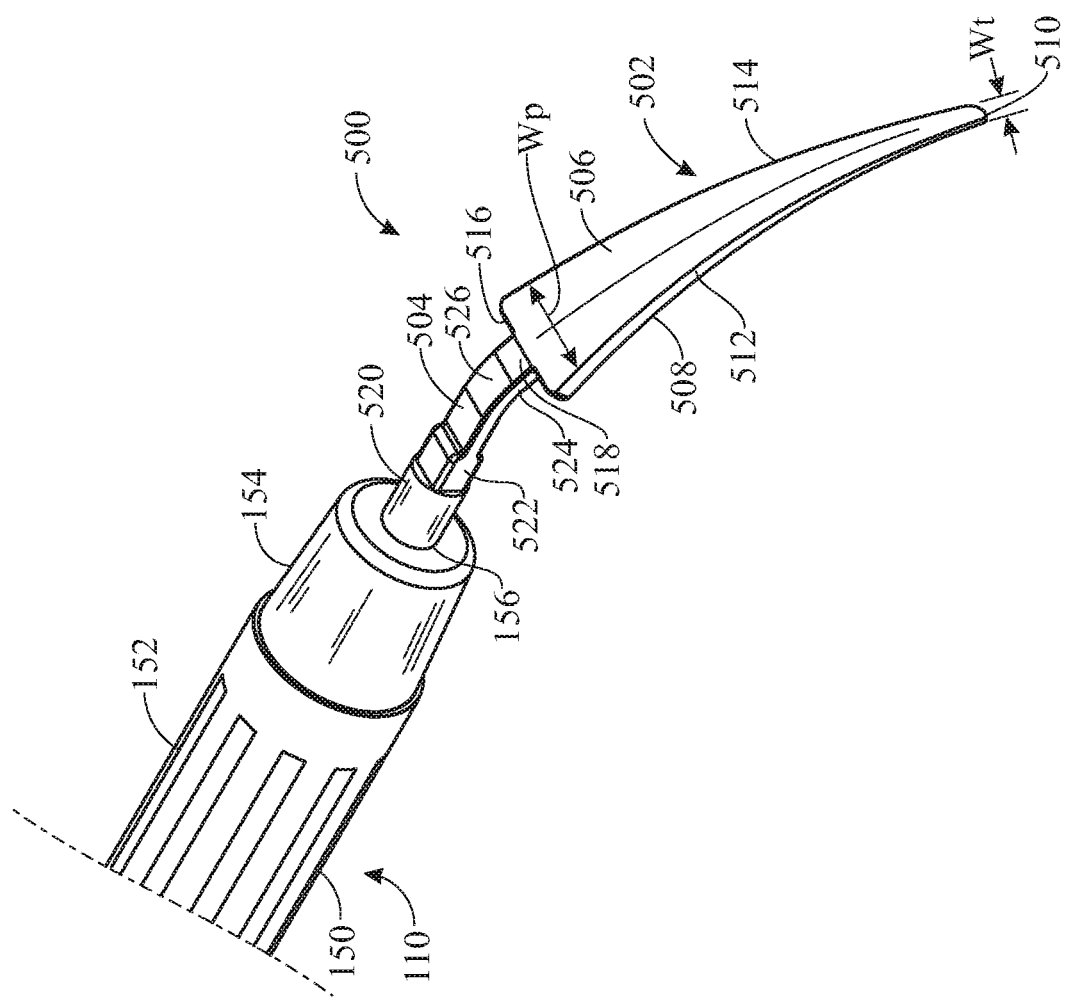
FIG. 9 presents a top, front isometric view of an ultrasonic, handheld tongue-cleaning tool comprising an ultrasonic hand piece carrying a fifth tongue-cleaning working tip in accordance with an illustrative embodiment of the present invention, for use in cleaning a patient's tongue.
Figure 10:
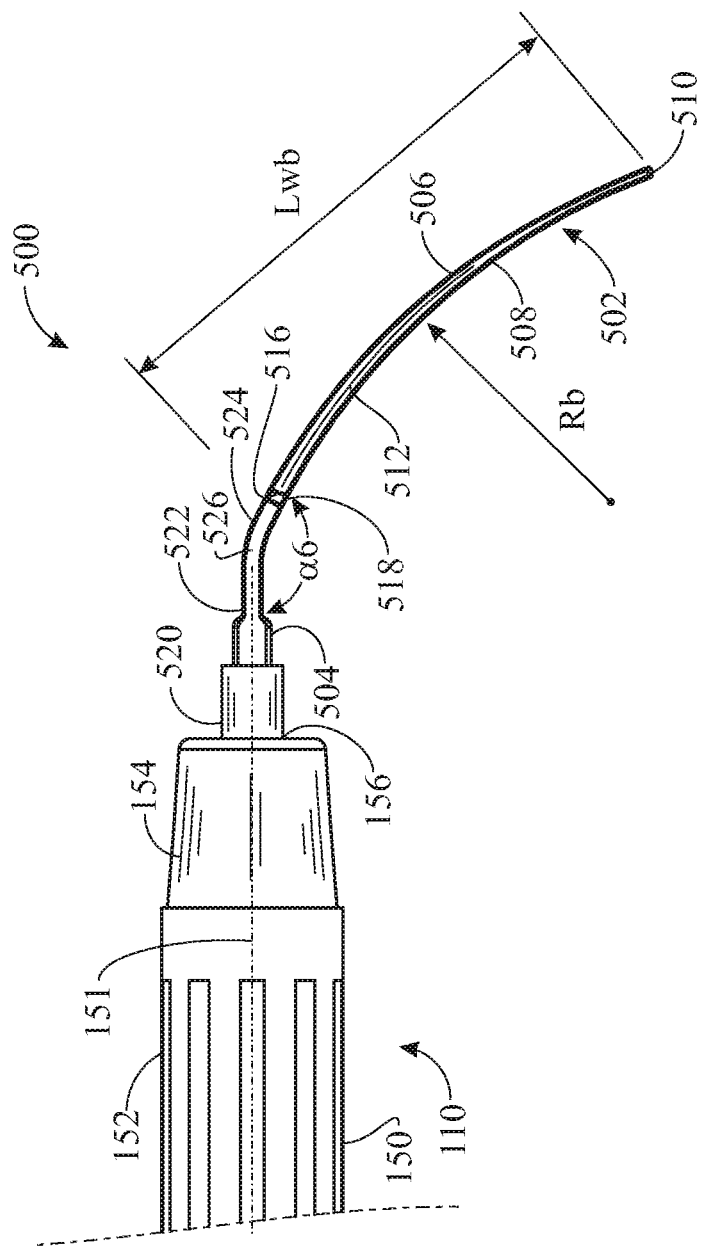
FIG. 10 presents a side elevation view of the tongue-cleaning tool of FIG. 9, illustrating the tongue-cleaning working tip and a distal portion of the hand piece.

Turning now to FIGS. 9 and 10 there is disclosed a fifth tongue-cleaning working tip 500 particularly configured to scrape corners and side edges of the tongue as far back as a user can reach. The tongue-cleaning working tip 500 generally includes a curved distal working blade 502 and a proximal mounting stem 504. The distal working blade 502 includes a convex upper surface 506 and a concave lower surface 508. The distal working blade 502 additionally includes a distal working tip or edge 510, first and second side edges 512 and 514, respectively, and a proximal edge 516. In some embodiments, the distal working blade 502 can optionally taper from its greatest width "Wp" at the proximal edge 516 to a smaller width "Wt" at the distal working edge 510. Thus, the first and second side edges 512 and 514 can angle toward each other from the proximal edge 516 to the distal working edge 510. The distal working edge 510, along with the first and second side edges 512 and 514, can be sharp or rounded. Though not shown, in some embodiments, the first and/or second side edges 512 and 514 can be curved or looped inward, similarly to the looped or curved distal portion 226 of the distal working blade 202 of the tongue-cleaning working tip 200 shown in FIGS. 3 and 4. Additionally, as shown in FIG. 10, the distal working blade 502 has downward curvature indicated schematically by a radius of "Rb" due to the concavity of the lower surface 508. The length "Lwb" of the working blade 502 can vary from ½ inch to about 2 inches, and preferably be approximately ¾ inch.

The proximal mounting stem 504 includes a distal end 518 coupled to the proximal edge 516 of the distal working blade 502 and a proximal end 520 coupled to the ultrasonic hand piece 110. The proximal mounting stem 504 includes a proximal stem portion 522 and a distal stem portion 524 extending from the proximal stem portion 522 through a stem bend 526 and at an angle α6, which is within the range from 10 to 175 degrees, and preferably from 60 to 160 degrees, and more preferably from 100 to 140 degrees. Thus, angle α6 also matches the average angle formed between the distal working blade 502 and the longitudinal direction 151 of the grasping portion 152 of the elongate body portion 150 of the ultrasonic hand piece 110.

Figure 11:
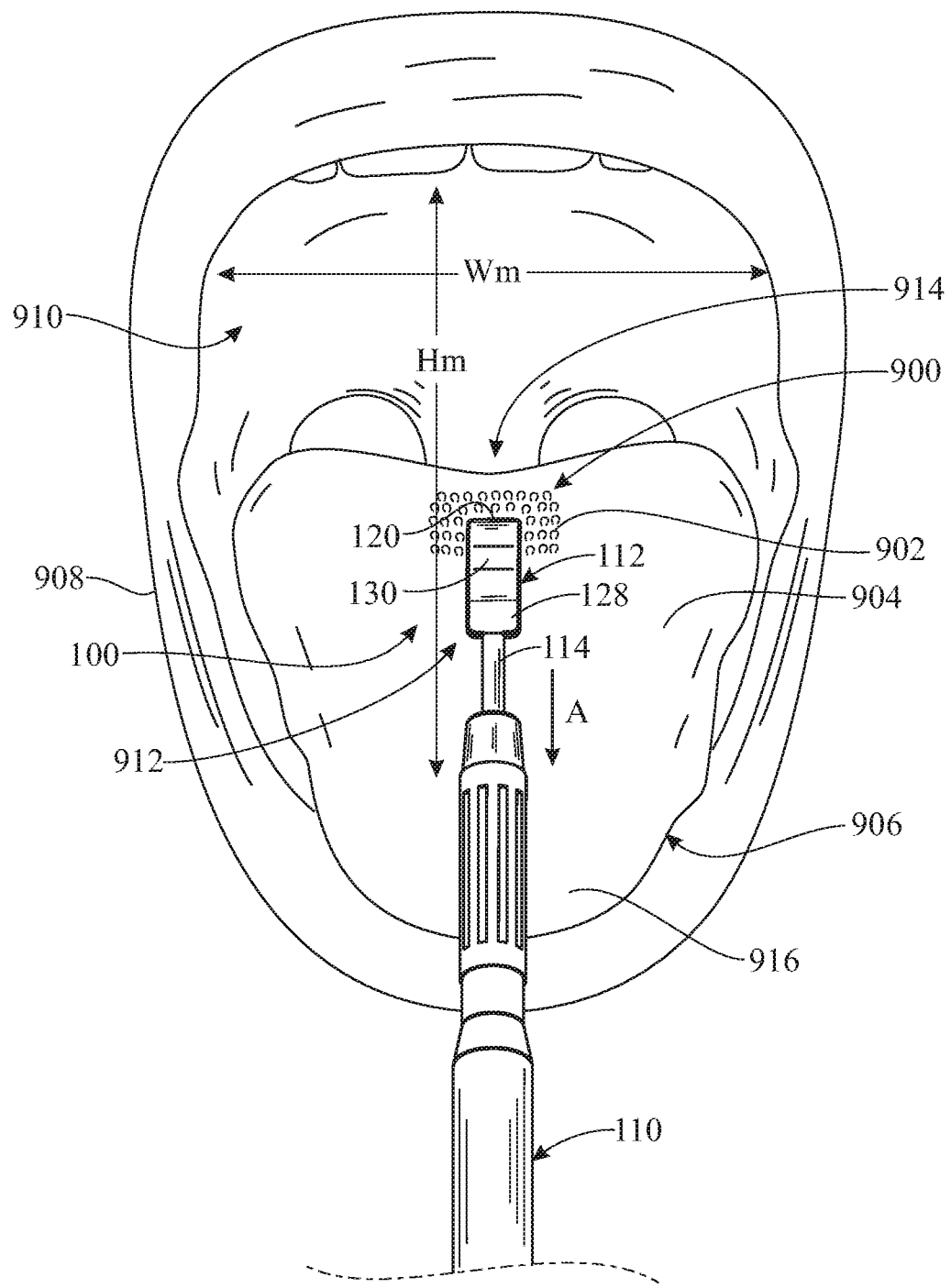
FIG. 11 presents a front view of the tongue-cleaning tool of FIGS. 1 and 2 in use to clean and scrape off a biofilm of anaerobic bacteria from mixed areas of a patient's tongue's anatomy including the middle of the tongue.

Referring now to FIGS. 11-15, and initially with regard to FIG. 11, the use of the various disclosed ultrasonic tongue-cleaning tips to scrape off the anaerobic bacteria containing biofilm in differing areas of a patient's tongue will now be described. As shown in FIG. 11, a tongue-cleaning tool including the first tongue-cleaning working tip 100 and the ultrasonic hand piece 110 is used to remove putrefying anaerobic bacteria 900 contained within a biofilm 902 of bacteria located on an upper surface 904 of a patient's tongue 906. The patient's tongue 906 is located within the patient's mouth 908 and is accessed by opening the mouth 908 to form a mouth opening 910. The mouth opening 910 has a maximum width "Wm" and a maximum height "Hm". As discussed above, the sizes of the various tongue-cleaning tools formed by the ultrasonic hand piece 110 and the various working tips are sized and shaped to easily fit within the mouth opening 910 and to be maneuvered inside the mouth 908.

To clean the anaerobic bacteria 900 off of the patient's tongue 906, the tongue-cleaning working tip 100 is inserted into the opening or connector 156 of the ultrasonic hand piece 110 and secured therein or coupled thereto in known manner (in other embodiments, the tongue-cleaning working tip 100 may be integrally formed with the ultrasonic hand piece 110). The ultrasonic hand piece 110 is then connected to a source of power and switched on to transmit vibrations in the ultrasonic frequency to the tongue-cleaning working tip 100. The tongue-cleaning tool is thus prepared to clean the anaerobic bacteria 900 off of an area of the tongue 906, for example, the middle 912 of the tongue 906.

The distal working edge 120 of the tongue-cleaning working tip 100 is positioned on the middle 912 of the tongue 906 and is pulled across the tongue 906 from a rear or posterior area 914 of the tongue 906 to a forward or anterior area 916 of the patient's tongue 906 in the direction of arrow "A", or in a direction opposite to arrow "A". The tool can also be moved to scrape sideways (i.e. in a left-to-right or right-to-left direction) or in an oblique direction which is a combination of a sideways and front-to-back or back-to-front movement. The ultrasonic vibrations transmitted to the distal working edge 120 allow the distal working edge 120 of the tongue-cleaning working tip 100 to cut into or otherwise breakup the biofilm 902 of putrefying anaerobic bacteria 900 and release it from the patient's tongue. As noted above, and while not specifically shown, the ultrasonic hand piece 110 may be provided with a source of cleaning or cooling fluid for transmission through the tongue-cleaning working tip 110. This allows the dislodged bacteria 900 to be flushed away and underlying tissues to be cooled.

It should be noted that several sessions of treatments may be necessary to avoid overheating or burning of the patient's tongue with the ultrasonic vibrations.

Figure 12:
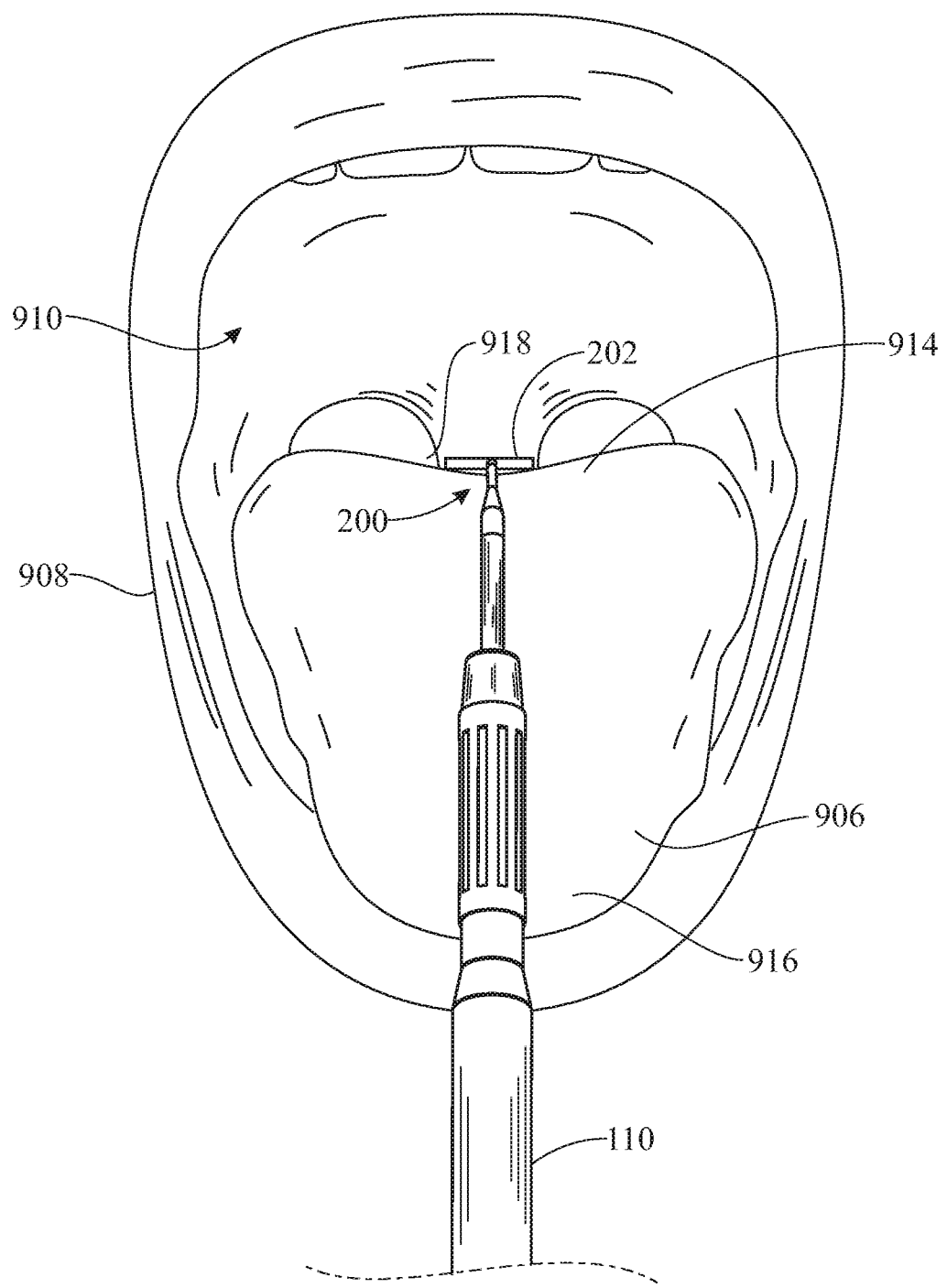
FIG. 12 presents a front view of the tongue-cleaning tool of FIGS. 3 and 4 in use to clean and scrape off the biofilm from a posterior most portion of a patient's tongue.

Referring now to FIG. 12, there is disclosed the use of a handheld, ultrasonic tongue-cleaning tool formed by the second tongue-cleaning working tip 200 and the hand piece 110 to clean the putrefying anaerobic bacteria from the posterior area 914 of the patient's tongue 906, i.e., in the last or furthest ⅓ to ⅕ of the patient's tongue 906. The tool is initially prepared as above, with the tongue-cleaning working tip 200 coupled to, or integrally formed with, the ultrasonic hand piece 110 and power provided to vibrate the tongue-cleaning working tip 200 in the ultrasonic range. The tongue-cleaning working tip 200 is inserted through the mouth opening 910 and the distal working blade 202 of the tongue-cleaning working tip 200 positioned on the most posterior area 914 of the patient's tongue 906 where the patient's tongue 906 connects to the patient's pharynx 918. The tongue-cleaning working tip 200 is then used as above to remove the putrefying anaerobic bacteria from posterior area 914 of the tongue 906. The curvature of the distal working blade 202 allows the operator to reach and access the most posterior area 914 of the tongue 906.

Figure 13:
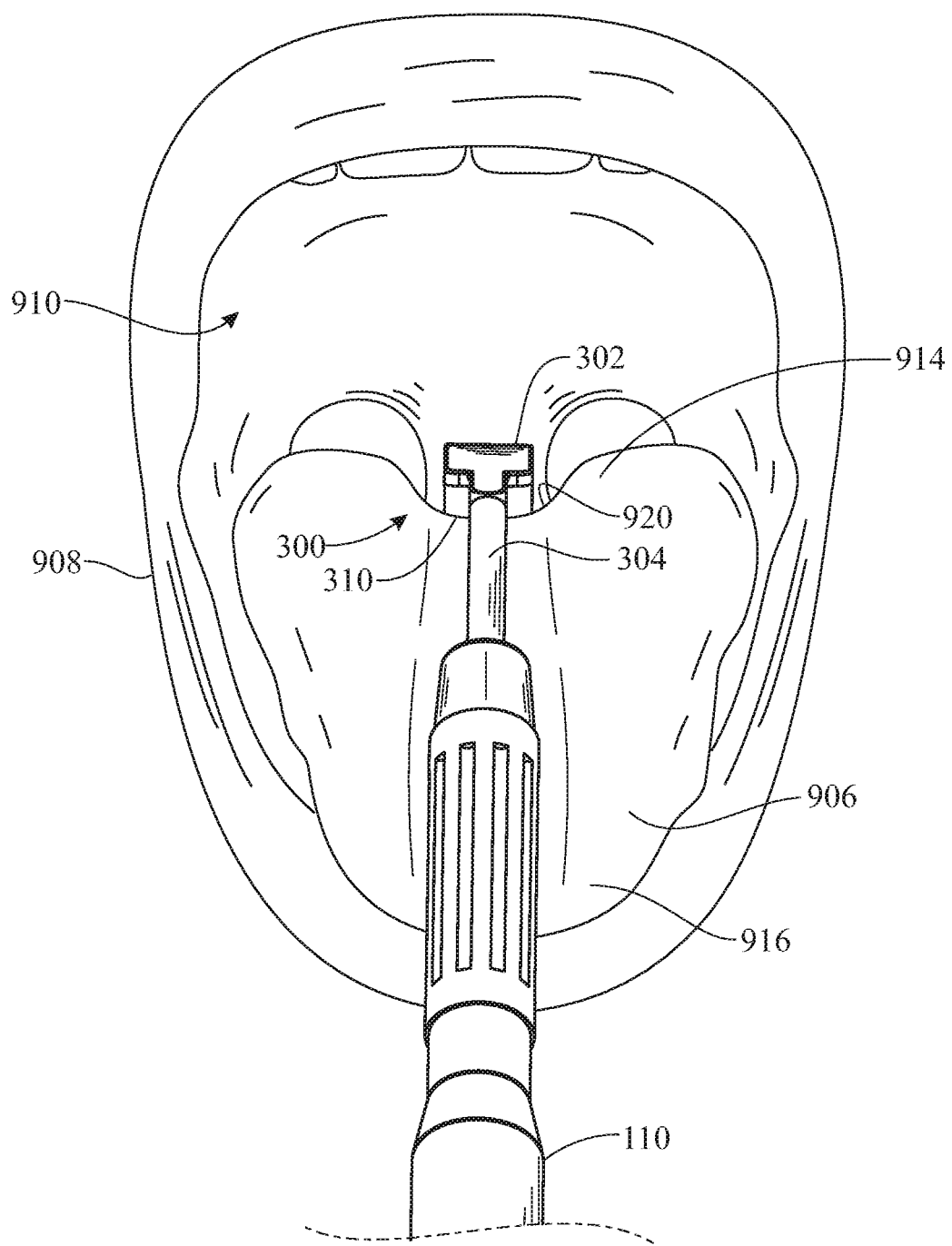
FIG. 13 presents a front view of the tongue-cleaning tool of FIGS. 5 and 6 in use to clean and scrape off the biofilm from concave areas of the patient's tongue.

Turning now to FIG. 13, a handheld, ultrasonic tongue-cleaning tool formed by hand piece 100 fitted with the third tongue-cleaning working tip 300 having the curved distal working edge 310 on the distal working blade 302 is illustrated cleaning the middle area 912 of the tongue 906. This tongue-cleaning working tip 300 is especially useful where a patient's tongue 906 is stuck all the way out and it is difficult to reach the middle area 912 of the tongue 906, especially at the posterior area 914. As depicted, when stuck out, the tongue 906 forms a depression or inward curvature 920 in the middle area 912 of the tongue 906 that can be adequately cleaned with the curved distal working edge 310 on the distal working blade 302 of the present, third tongue-cleaning working tip 300.

As with the remaining working tips, the tongue-cleaning working tip 300 is prepared with the ultrasonic hand piece 110 as above and is inserted through the mouth opening 910 to access that area of the tongue 906. The distal working blade 302 of the tongue-cleaning working tip 300 is positioned such that the curved distal working edge 310 rides along and within the curve 920 in the tongue 906 as the tongue-cleaning working tip 300 is pulled from the posterior area 914 of the tongue 906 to the anterior area 916 to scrape away and dislodge the putrefying anaerobic bacteria. The angle α2 of the distal working blade 302 (FIG. 6) allows the distal working edge 310 to reach down into the tongue 906.

Figure 14:
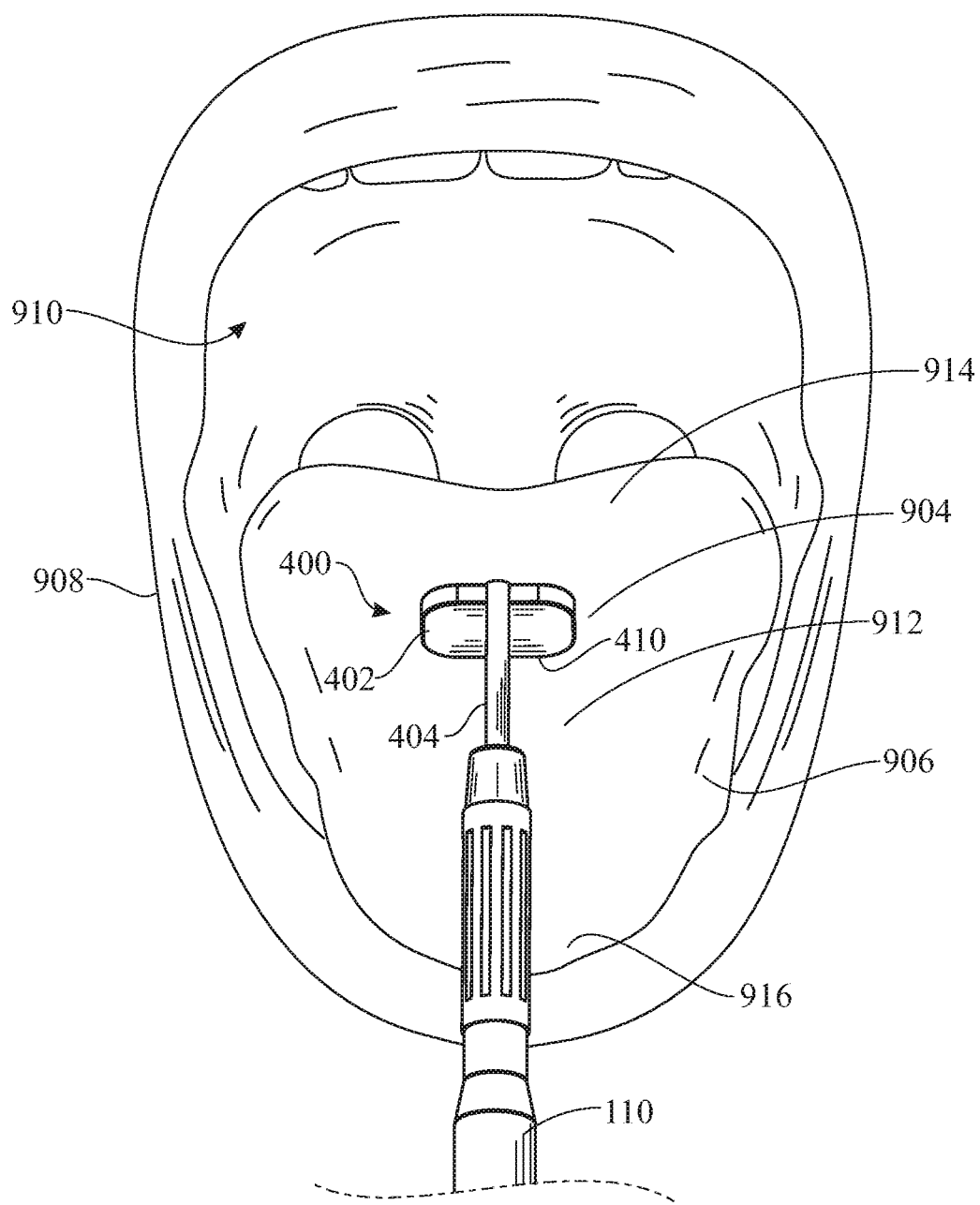
FIG. 14 presents a front view of the tongue-cleaning tool of FIGS. 7 and 8 in use to clean and scrape off the biofilm from anterior areas of the patient's tongue.

Referring now to FIG. 14, there is disclosed the use of a handheld, ultrasonic tongue-cleaning tool formed by the fourth tongue-cleaning working tip 400 and the hand piece 110. The fourth tongue-cleaning working tip 400 is best utilized to clean the anterior two-thirds to four-fifths of the tongue 906. The tongue-cleaning working tip 400 is prepared with, or integrally formed with, the ultrasonic hand piece 110 and is inserted into the patient's mouth 908 to position the distal working edge 410 of the distal working blade 402 on the upper surface 904 of the patient's tongue 906. The fourth tongue-cleaning working tip 400 is best suited for cleaning this area of the tongue 906 due to the increased size and ability to scrape larger area of the tongue 906 as opposed to some of the more specialized and narrower disclosed tongue-cleaning working tools.

Figure 15:
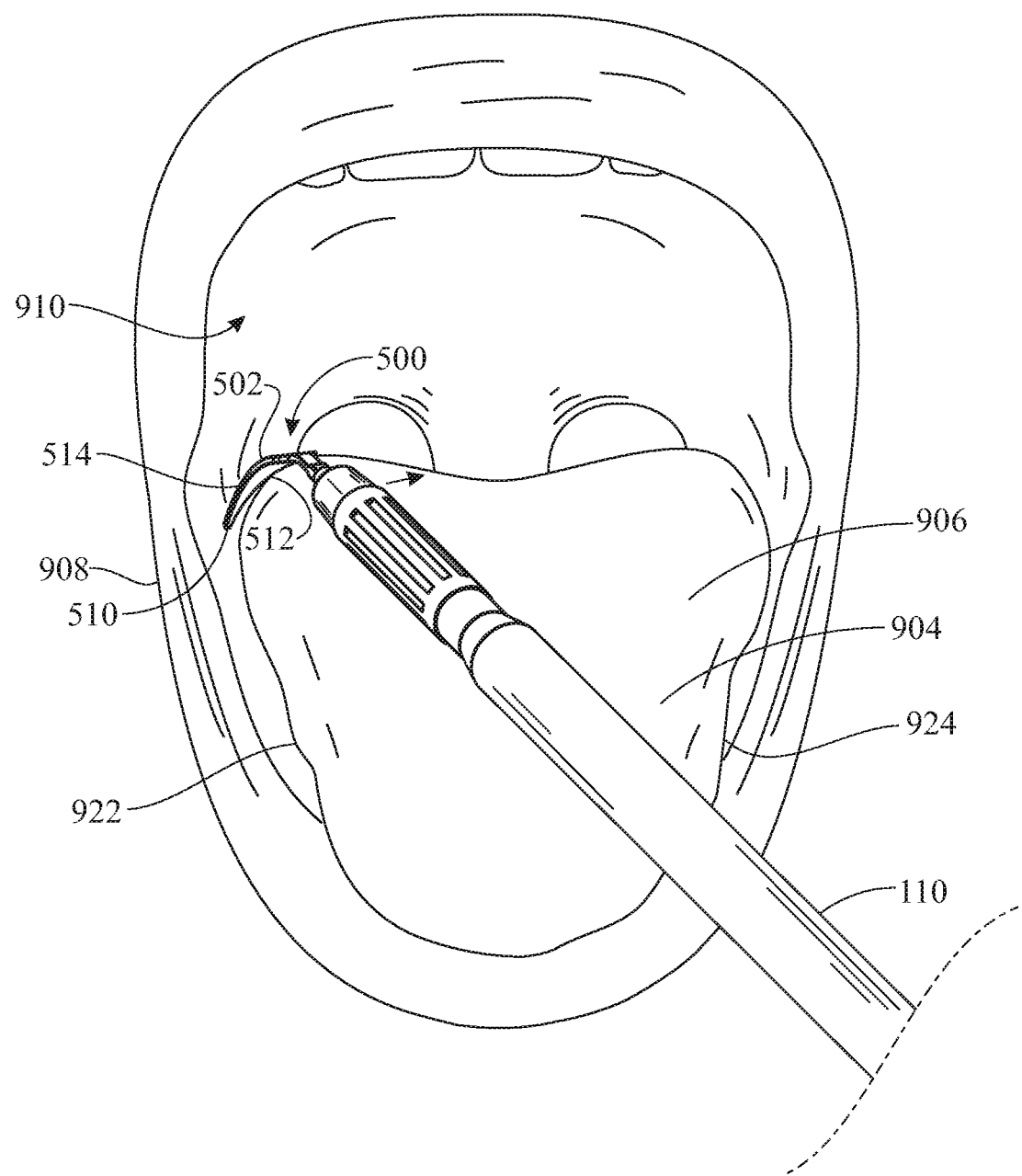
FIG. 15 presents a front view of the tongue-cleaning tool of FIGS. 9 and 10 in use to clean and scrape off the biofilm from sides and corners of the patient's tongue.

Turning to FIG. 15, there is disclosed the use of a handheld, ultrasonic tongue-cleaning tool formed by the fifth tongue-cleaning working tip 500 and the hand piece 110. In order to access and scrape the sides of the tongue and corners of the tongue as far back as the tongue-cleaning kit can reach, it is desirable to use the narrower and more curved, fifth tongue-cleaning working tip 500 having the arcuate distal working blade 502 terminating in the narrow distal working edge 510. Additionally, the arcuate or curved first and second side edges 512 and 514 facilitate scraping right and left side edges 922 and 924 of the patient's tongue 906.

In the disclosed illustration, the tool has been prepared by coupling the tongue-cleaning working tip 500 to the ultrasonic hand piece 110 (unless they are integrally formed) and positioned such that the first side edge 512 of the distal working blade 502 is positioned to scrape the right side edge 922 of the patient's tongue 906. The process is similar to that described herein above in that the power is turned on to transmit vibrations in the ultrasonic frequency to the distal working edge 510 and the first and second side edges 512 and 514, respectively, of the distal working blade 502 and using those edges to reach and scrape putrefying anaerobic bacteria 900 off of the patient's tongue 906. As shown, the tongue-cleaning working tip 500 is rotated leftwards so that the first side edge 512 of the curved working tip conforms to right side 922 of the tongue 906 while scraping the surface of the right side 922 of the tongue 906. Similarly, the tongue-cleaning working tip 500 shall be rotated towards the right so that the second side edge 514 of the curved working tip conforms to left side 924 of the tongue 906 while scraping the surface of left side 924 the tongue 906.

In this manner, the tongue-cleaning working tips 100, 200, 300, 400 and 500 along with a set of one or more ultrasonic hand piece or pieces (e.g., piezoelectric or magnetostrictive hand piece(s)) form a useful and novel tongue-cleaning tool kit for removing the biofilm 902 of putrefying anaerobic bacteria 900 from the upper surface 904 and right and left sides 922 and 924 of a patient's tongue 906 to minimize the occurrence of the malodorous emissions causing bad breath.

In some embodiments, the tongue-cleaning working tips may vibrate in the sonic range, in addition to or instead of the ultrasonic range of frequencies. For example, the handheld piece may generate a sonic vibration causing the working tip to vibrate in the sonic range. Alternatively, the handpiece may generate an ultrasonic vibration which slows down to a sonic vibration when being transferred to the working tip.

Alternative embodiments are contemplated to those depicted herein. For instance, the length and/or width of the working tips may vary without departing from the scope of the claims.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A tongue-cleaning tool kit for removing a biofilm from a surface of a tongue, the tongue-cleaning tool kit comprising a plurality of tongue-cleaning working tips, each working tip of the tongue-cleaning working tips comprising a respective distal working blade configured to scrape a biofilm from a surface of a tongue, the tongue-cleaning working tips including:

an angled, tongue-cleaning working tip, the distal working blade of which is elongated in a front-to-back, longitudinal direction and comprises a planar, proximal blade portion and a planar, distal blade portion connected to the proximal blade portion at a bend portion and arranged forming a forward angle relative to the proximal blade portion, wherein the proximal blade portion and the distal blade portion of the angled, tongue-cleaning working tip each include a first side edge and a second side edge extending longitudinally and parallel to one another, and the distal blade portion includes a straight front scraping edge normal to the first and second side edges and having rounded corners where the parallel first and second side edges of the proximal and distal blade portion meet the straight front scraping edge of the distal blade portion, wherein the proximal and distal blade portion includes a top and a bottom surface that are flat and smooth, and wherein the first and second side edges and the straight front scraping edge are rounded; and a curved, tongue-cleaning working tip, the distal working blade of which is curved and comprises a convex top surface and a concave bottom surface.

2. The tongue-cleaning working kit of claim 1, wherein the distal blade portion of the angled, tongue-cleaning working tip is longer than the proximal blade portion of the angled, tongue-cleaning working tip.

3. The tongue-cleaning working kit of claim 1, wherein the distal working blade of the angled, tongue-cleaning working tip is formed as an angled plate having a constant thickness and the top and bottom surfaces are separated by the constant thickness.

4. The tongue-cleaning working kit of claim 1, wherein the distal working blade of the angled, tongue-cleaning working tip extends distally from a proximal mounting stem.

5. The tongue-cleaning working kit of claim 4, wherein the proximal mounting stem comprises a proximal end extending in a same direction as the proximal blade portion of the angled, tongue-cleaning working tip.

6. The tongue-cleaning working kit of claim 5, wherein the proximal mounting stem is straight and extends in the same direction from the proximal end of the proximal mounting stem to a distal end of the proximal mounting stem which is connected to the proximal blade portion of the angled, tongue-cleaning working tip.

7. The tongue-cleaning working kit of claim 4, wherein the proximal mounting stem comprises a proximal end arranged forming an angle with the proximal blade portion of the angled, tongue-cleaning working tip.

8. The tongue-cleaning working kit of claim 7, Wherein the proximal mounting stem comprises a proximal stem portion and a distal stem portion forming an angle with one another, wherein the proximal stem portion provides the proximal end of the proximal mounting stem and the distal stem portion is connected to and arranged in a same direction with the proximal blade portion of the angled, tongue-cleaning working tip.

9. The tongue-cleaning working kit of claim 1, wherein the distal working blade of the curved, tongue-cleaning working tip has a varying radius of curvature.

10. The tongue-cleaning working kit of claim 9, wherein the distal working blade of the curved, tongue-cleaning working tip comprises a distal working tip which is curved rearwardly towards a proximal end of said distal working blade of the curved, tongue-cleaning working tip.

11. The tongue-cleaning working kit of claim 1, wherein the plurality of, tongue-cleaning working tips further comprises a flat, tongue-cleaning working tip, the distal working blade of which is a plate that is rectangularly-shaped having rounded corners and rounded plate edges.

12. The tongue-cleaning working kit of claim 11, wherein the distal working blade of the flat, tongue-cleaning working tip extends distally from a proximal mounting stem.

13. The tongue-cleaning working kit of claim 12, wherein the proximal mounting stem comprises a proximal stem portion and a distal stem portion forming an angle with one another, wherein the proximal stem portion provides a proximal end of the proximal mounting stem and the distal stem portion is connected to and arranged in a same direction with the proximal blade portion of the flat, tongue-cleaning working tip.

14. The tongue-cleaning working kit of claim 1, wherein the distal working blade of the curved, tongue-cleaning working tip provides an uninterrupted thickness separating, a smooth top convex surface and a smooth concave bottom surface, and wherein the working tip is tapered from a wider proximal edge to a narrower distal edge thereof.

15. The tongue-cleaning tool kit of claim 1, further comprising a hand piece configured to carry one or more working tips of the at least one tongue-cleaning working tip, the hand piece further configured to produce ultrasonic and/or sonic vibrations and transfer the vibrations to the one or more working tips.

16. The tongue-cleaning tool kit of claim 15, wherein the hand piece is piezoelectric.

17. The tongue-cleaning tool kit of claim 15, wherein the hand piece is magnetostrictive.

18. A tongue-cleaning tool kit for removing a biofilm from a surface of a tongue, the tongue-cleaning tool kit comprising a plurality of tongue-cleaning working tips, each working tip of the tongue-cleaning working tips comprising a respective distal working blade configured to scrape a biofilm from a surface of a tongue, the tongue-cleaning working tips including:

an angled, tongue-cleaning working tip, the distal working blade of which is elongated in a front-to-back, longitudinal direction and comprises a planar, proximal blade portion and a planar, distal blade portion connected to the proximal blade portion at a bend portion and arranged forming a forward angle relative to the proximal blade portion, wherein the proximal blade portion and the distal blade portion of the angled, tongue-cleaning working tip each include a first side edge and a second side edge extending longitudinally and parallel to one another, and the distal blade portion includes a straight front scraping edge normal to the first and second side edges and having rounded corners where the parallel first and second side edges of the proximal and distal blade portion meet the straight front scraping edge of the distal blade portion, wherein the proximal and distal blade portion includes a top and a bottom surface that are flat and smooth, and wherein the first and second side edges and the straight front scraping edge are rounded;

a curved, tongue-cleaning working tip, the distal working blade of which is curved and comprises a convex top surface and a concave bottom surface; and a flat, tongue-cleaning working tip; the distal working blade of which is a plate that is rectangularly-shaped having rounded corners and rounded plate edges.

19. A tongue-cleaning tool kit for removing a biofilm from a surface of a tongue, the tongue-cleaning tool kit comprising a plurality of tongue-cleaning working tips, each working tip of the tongue-cleaning working tips comprising a respective distal working blade configured to scrape a biofilm from a surface of a tongue; the tongue-cleaning working tips including:

a first angled, tongue-cleaning working tip, the distal working blade of which is elongated in a front-to-back, longitudinal direction and comprises a planar, proximal blade portion and a planar, distal blade portion connected to the proximal blade portion at a bend portion and arranged forming a forward angle relative to the proximal blade portion, wherein the proximal blade portion and the distal blade portion of the angled, tongue-cleaning working tip each include a first side edge and a second side edge extending longitudinally and parallel to one another, and the distal blade portion includes a straight front scraping edge normal to the first and second side edges and having rounded corners where the parallel first and second side edges of the proximal and distal blade portion meet the straight front scraping edge of the distal blade portion, wherein the proximal and distal blade portion includes a top and a bottom surface that are flat and smooth, wherein the first and second side edges and the straight front scraping edge are rounded, and wherein the proximal blade portion of the first angled, tongue-cleaning working tip extends from a straight, proximal mounting stem in a same direction as the proximal mounting stem;

a second angled, tongue-cleaning working tip, the distal working blade of which is elongated in a front-to-back, longitudinal direction and comprises a planar, proximal blade portion and a planar, distal blade portion connected to the proximal blade portion at a bend portion and arranged forming an angle relative to the proximal blade portion, wherein the proximal blade portion of the second angled, tongue-cleaning working tip extends from an angled, proximal mounting stem comprising a proximal stem portion and a distal stem portion forming an angle with one another;

a flat, tongue-cleaning working tip, the distal working blade of which is a plate that is rectangularly-shaped having rounded corners and rounded plate edges;

a first curved, tongue-cleaning working tip, the distal working blade of which is curved, comprises a convex top surface and a concave bottom surface, and comprises a distal working tip which is curved rearwardly towards a proximal end of said distal working blade of the first curved, tongue-cleaning working tip, wherein the working blade is rectangularly-shaped having at least two rounded corner edges; and a second curved, tongue-cleaning working tip, the distal working blade of which is curved, having an uninterrupted thickness separating a smooth convex top surface and a smooth concave bottom surface, and wherein the second curved working tip is tapered from a wider proximal edge to a narrower distal edge of said distal working blade.

* * * * *